(12) United States Patent
Jonkman

(10) Patent No.: US 8,377,036 B2
(45) Date of Patent: Feb. 19, 2013

(54) CANNULA REINFORCING BAND AND METHOD

(75) Inventor: Kenneth R. Jonkman, Marne, MI (US)

(73) Assignee: Avalon Laboratories, Inc., Rancho Dominguez, CA (US)

( * ) Notice: Subject to any disclaimer, the term of this patent is extended or adjusted under 35 U.S.C. 154(b) by 408 days.

(21) Appl. No.: 12/145,798

(22) Filed: Jun. 25, 2008

(65) Prior Publication Data

US 2009/0076482 A1    Mar. 19, 2009

Related U.S. Application Data

(60) Provisional application No. 60/972,479, filed on Sep. 14, 2007.

(51) Int. Cl.
*A61M 25/00* (2006.01)

(52) U.S. Cl. ........ 604/526; 604/523; 604/524; 604/525; 604/533; 604/534; 604/535; 604/536; 604/537; 604/538; 604/539; 604/284; 600/139; 600/140; 600/144

(58) Field of Classification Search .......... 604/523–527, 604/264, 533–284; 600/139, 140, 144
See application file for complete search history.

(56) References Cited

U.S. PATENT DOCUMENTS

| | | | |
|---|---|---|---|
| 3,630,207 A * | 12/1971 | Kahn et al. | 604/524 |
| 4,037,599 A | 7/1977 | Raulerson | |
| 4,270,535 A | 6/1981 | Bogue et al. | |
| 4,493,696 A | 1/1985 | Uldall | |
| 4,547,193 A | 10/1985 | Rydell | |
| 4,548,597 A | 10/1985 | Nelson | |
| 4,639,252 A * | 1/1987 | Kelly et al. | 604/541 |
| 4,666,426 A | 5/1987 | Aigner | |
| 5,009,636 A | 4/1991 | Wortley et al. | |
| 5,053,004 A | 10/1991 | Markel et al. | |
| 5,209,723 A | 5/1993 | Twardowski et al. | |
| 5,324,253 A | 6/1994 | McRea et al. | |
| 5,346,471 A | 9/1994 | Raulerson | |
| 5,350,358 A | 9/1994 | Martin | |
| 5,405,320 A | 4/1995 | Twardowski et al. | |
| 5,480,380 A | 1/1996 | Martin | |
| 5,531,719 A * | 7/1996 | Takahashi | 604/525 |
| 5,718,678 A | 2/1998 | Fleming, III | |
| 5,769,828 A * | 6/1998 | Jonkman | 604/526 |
| 5,947,940 A | 9/1999 | Beisel | |
| 5,961,485 A | 10/1999 | Martin | |
| 5,976,103 A | 11/1999 | Martin | |
| 5,989,206 A | 11/1999 | Prosl | |
| 6,001,056 A | 12/1999 | Jassawalla et al. | |

(Continued)

FOREIGN PATENT DOCUMENTS

EP    1649889 A1    4/2006
WO    0025849    5/2000

*Primary Examiner* — Bhisma Mehta
*Assistant Examiner* — Larry R Wilson
(74) *Attorney, Agent, or Firm* — Price Heneveld LLP

(57) ABSTRACT

A cannula assembly having a hollow elongate cannula with a proximal end, a distal end, and a central axis. A coiled reinforcing member is disposed along a portion of the hollow elongate cannula and is adapted to provide structural support to the elongate cannula. An intermediate reinforcing band is disposed on the elongate cannula between the proximal end and the distal end to reinforce a perforated section in the wall of the cannula and includes a forward edge, a rearward edge, at least one rib and at least one protrusion extending orthogonally from the forward edge and at least one protrusion extending from the rearward edge. A distal reinforcing band is disposed at the distal end of the elongate cannula and has a plurality of fingers that taper slightly inwardly toward the central axis of the hollow elongate cannula.

20 Claims, 9 Drawing Sheets

U.S. PATENT DOCUMENTS

| | | | |
|---|---|---|---|
| 6,007,478 A * | 12/1999 | Siess et al. ................. 600/16 |
| 6,083,260 A | 7/2000 | Aboul-Hosn |
| 6,110,139 A | 8/2000 | Loubser |
| 6,113,568 A | 9/2000 | Olaussen |
| 6,123,725 A | 9/2000 | Aboul-Hosn |
| 6,383,172 B1 | 5/2002 | Barbut |
| 6,454,997 B1 | 9/2002 | Divino, Jr. et al. |
| 6,589,227 B2 | 7/2003 | Sonderskov Klint |
| 6,596,235 B2 | 7/2003 | Divino, Jr. et al. |
| 6,602,468 B2 | 8/2003 | Patterson et al. |
| 6,620,118 B1 | 9/2003 | Prosl et al. |
| 6,673,039 B1 | 1/2004 | Bridges et al. |
| 6,682,498 B2 | 1/2004 | Ross |
| 6,759,008 B1 | 7/2004 | Patterson et al. |
| 6,858,001 B1 | 2/2005 | Aboul-Hosn |
| 6,942,635 B2 | 9/2005 | Rosenblatt et al. |
| 6,969,379 B1 | 11/2005 | Aboul-Hosn |
| 6,976,979 B2 * | 12/2005 | Lawrence et al. ............ 604/524 |
| 7,135,008 B2 | 11/2006 | O'Mahoney et al. |
| 2002/0165600 A1 | 11/2002 | Banas et al. |
| 2003/0078564 A1 | 4/2003 | Viitala |
| 2004/0210180 A1 | 10/2004 | Altman |
| 2005/0004504 A1 | 1/2005 | Frye et al. |
| 2005/0085761 A1 | 4/2005 | Wang et al. |
| 2005/0228212 A1 | 10/2005 | Aboul-Hosn |
| 2005/0279370 A1 | 12/2005 | Aboul-Hosn |
| 2006/0100565 A1 | 5/2006 | Aboul-Hosn |
| 2007/0049902 A1 * | 3/2007 | Griffin et al. ................. 604/523 |

* cited by examiner

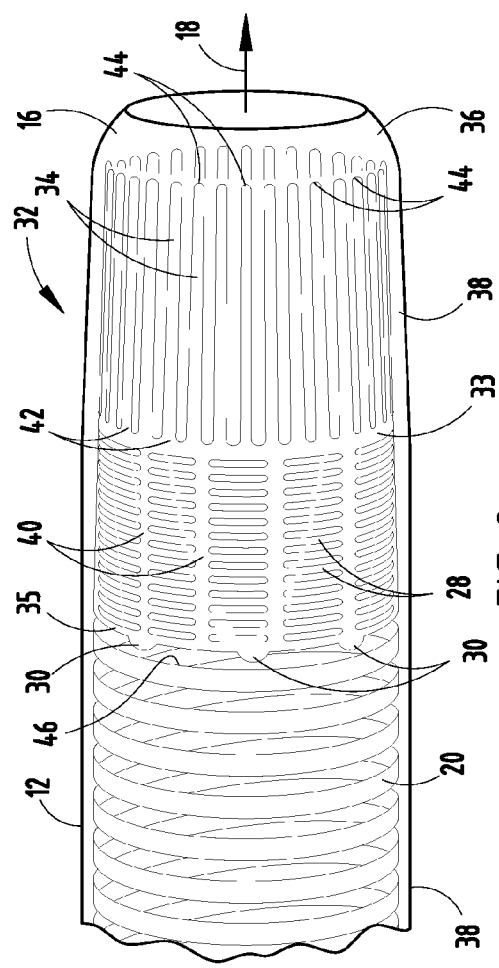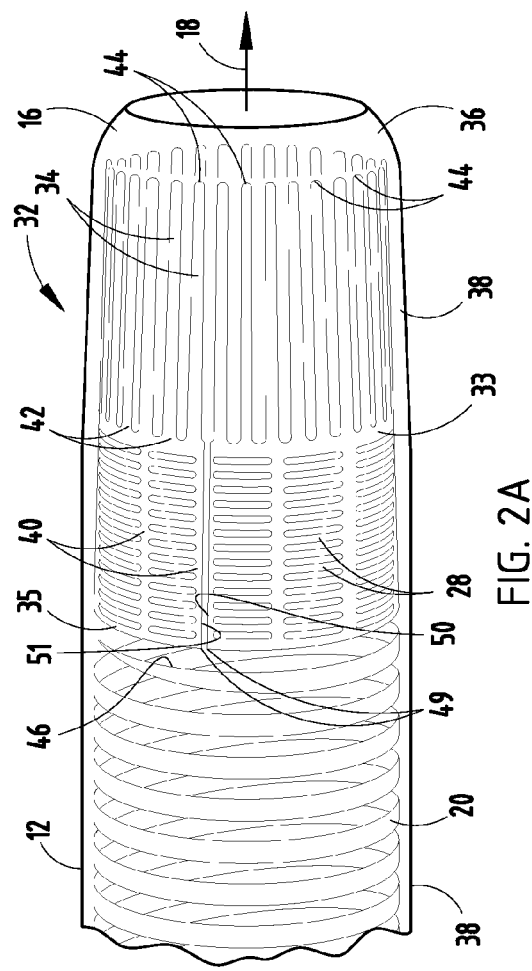

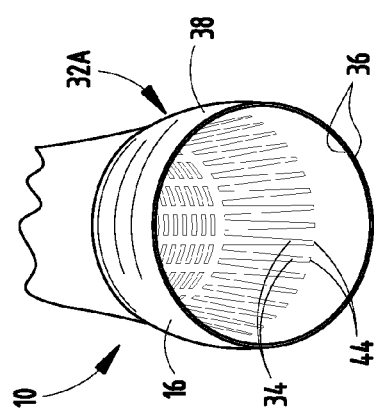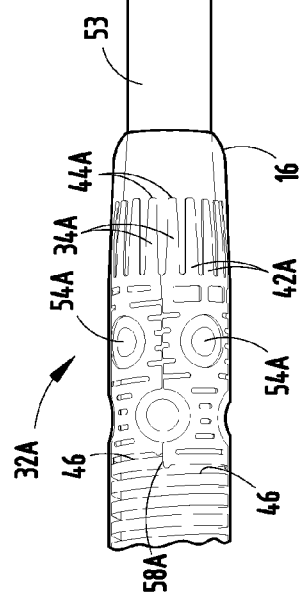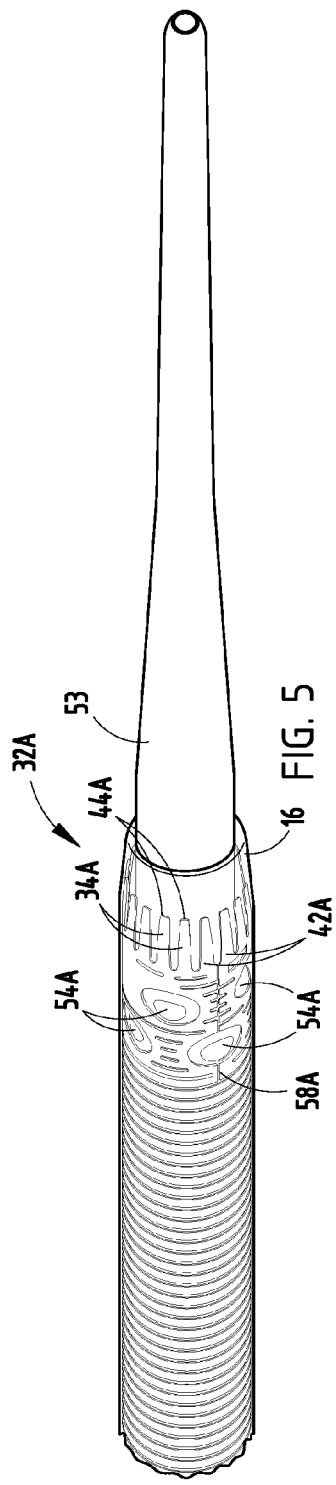

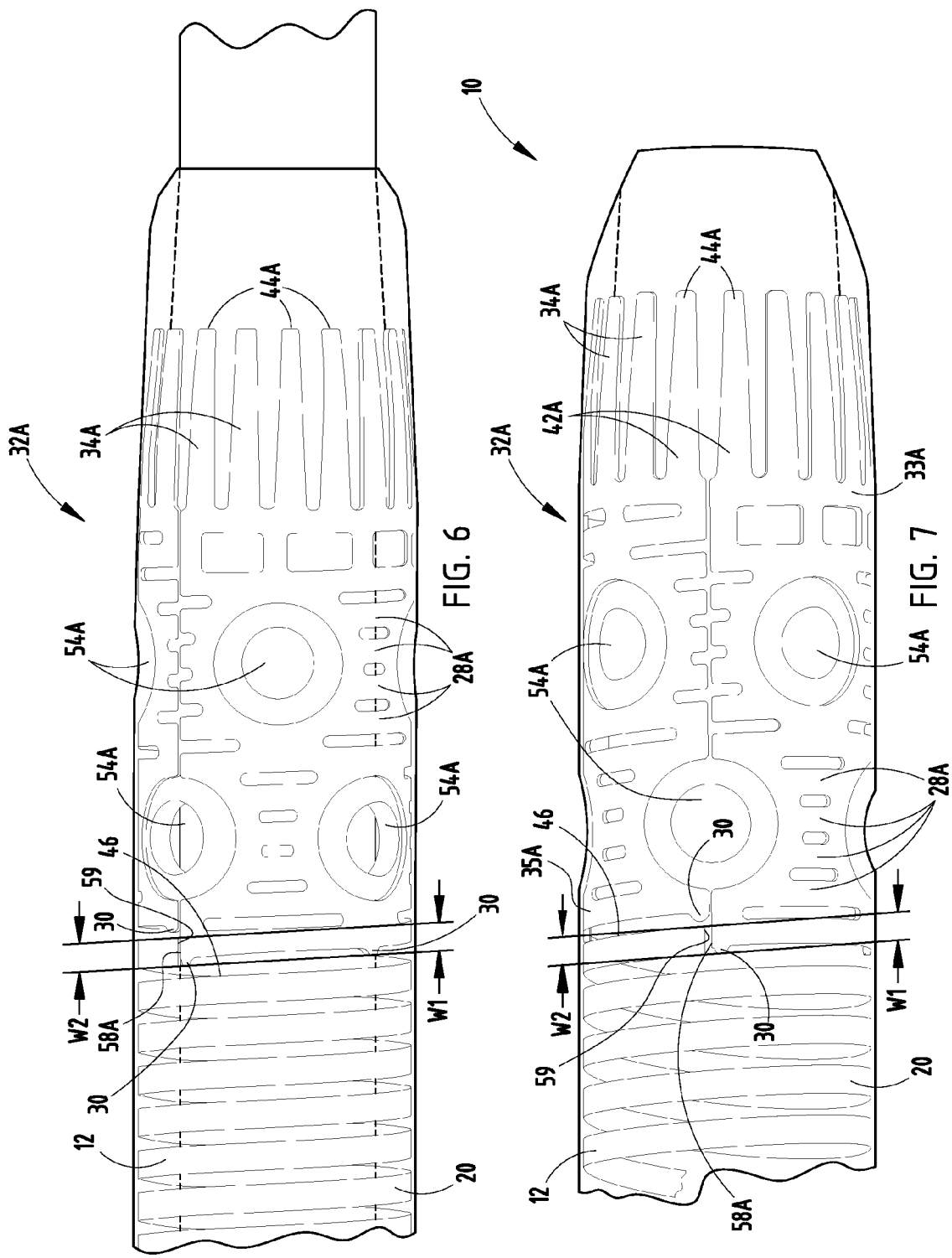

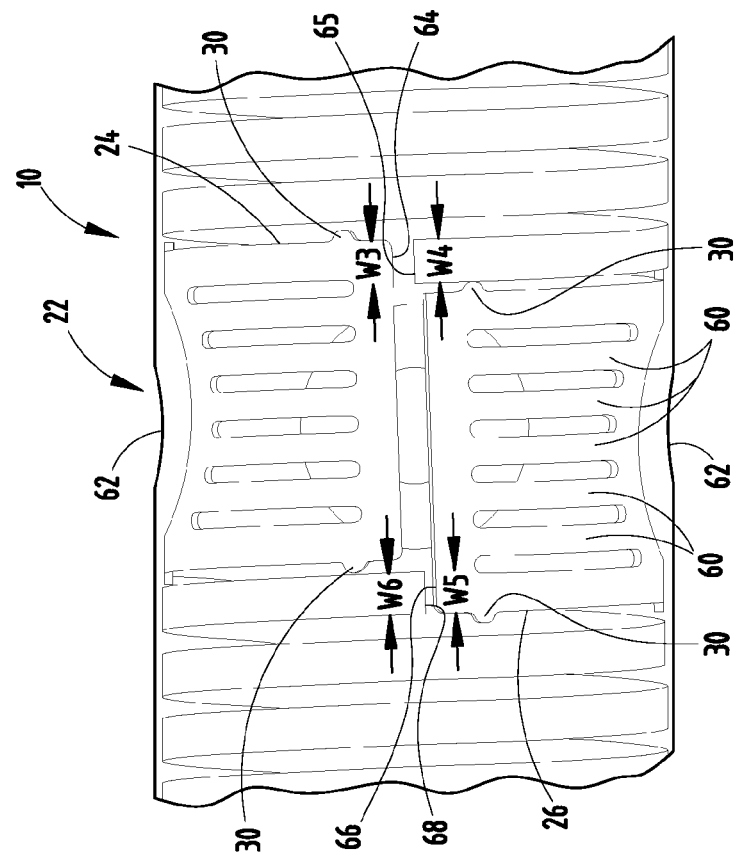
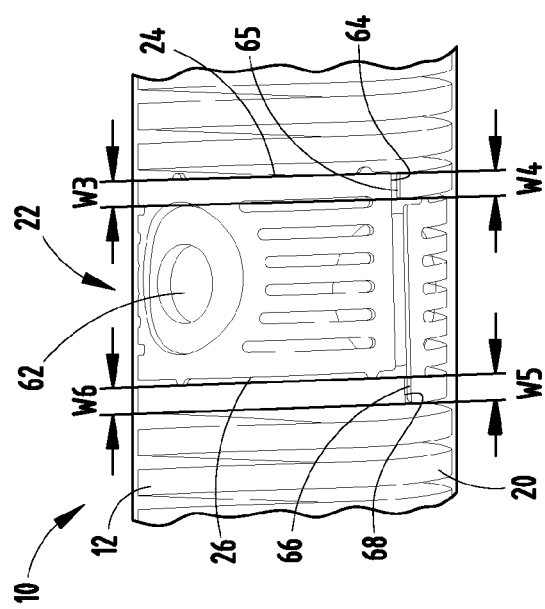
FIG. 12
FIG. 11

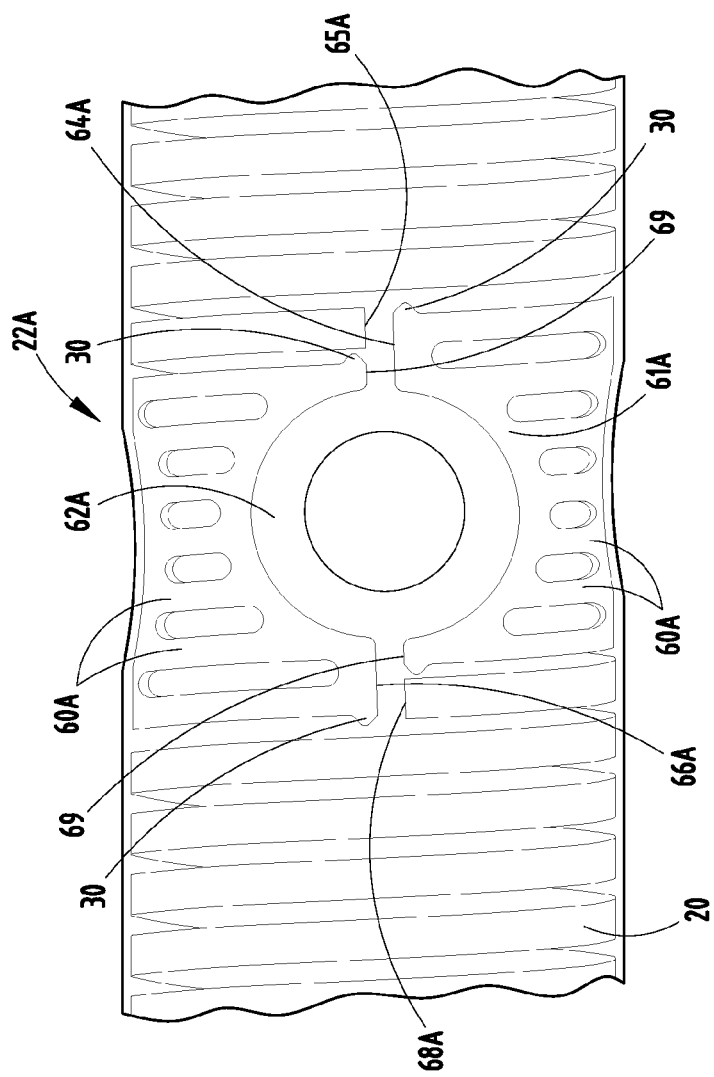
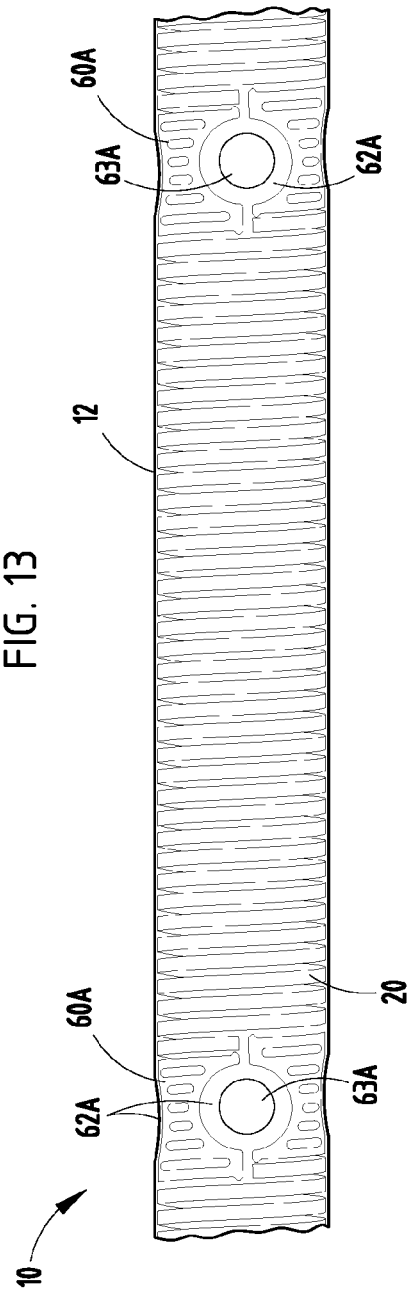
FIG. 13
FIG. 14

US 8,377,036 B2

CANNULA REINFORCING BAND AND METHOD

CROSS REFERENCE TO RELATED APPLICATION

This application claims benefit under 35 U.S.C. §119(e) of provisional application Ser. No. 60/972,479, filed Sep. 14, 2007, entitled CANNULA REINFORCING BAND AND METHOD. This application is also related to application Ser. No. 12/145,763, entitled INTRODUCER FOR CANNULA AND METHOD, filed on Jun. 25, 2008, and application Ser. No. 12/145,738, entitled COAXIAL VENAL CANNULA AND METHOD, filed on Jun. 25, 2008. The entire contents of each of the aforementioned applications are incorporated herein by reference.

BACKGROUND OF THE PRESENT INVENTION

The present invention relates to a cannula reinforcement member and the like, and in particular to a cannula reinforcement member for use at intermediate and distal ends of a cannula and a method related to the same.

During surgical operations, a physician frequently uses a cannula to assist in the removal of deoxygenated blood and introduction of oxygenated blood to the patient. The cannula is inserted into a blood vessel inside the patient's body until the cannula reaches a desired location. Because the blood vessels in the patient's body oftentimes follow a non-linear contour, a flexible cannula is desired. However, increased flexibility can lead to kinking and buckling.

Accordingly, a cannula having high flexibility while maintaining structural integrity is desired.

SUMMARY OF THE INVENTION

One aspect of the present invention is a distal basket for a cannula assembly including a cylindrical body portion installed in the cannula assembly and having a circular first edge, a circular second edge, and a central axis extending through the cylindrical body portion. At least one rib is disposed between the circular first edge and the circular second edge and extends substantially parallel with the first and second edges. A plurality of fingers extend orthogonally from the first edge. Each of the plurality of fingers has a base and a distal end.

Another aspect of the present invention is a distal basket for a cannula assembly including a cylindrical body portion installed in the cannula assembly and having a first edge, a second edge, and a central axis extending through the cylindrical body portion. At least one protrusion extends orthogonally from the second edge. At least one rib is disposed between the first edge and the second edge and extends substantially parallel with the first and second edges. A plurality of fingers extend orthogonally from the first edge. Each of the plurality of fingers has a base and a distal end.

Yet another aspect of the present invention includes an intermediate basket for a cannula assembly having a cylindrical body portion with a first edge, a second edge, and a central axis. At least one rib is disposed between the first edge and the second edge, has a predetermined width, and extends between the first and second edges. At least one port has an aperture extending orthogonally to the central axis.

Yet another aspect of the present invention is a cannula assembly having a hollow elongate cannula with a proximal end, a distal end, and a central axis. A first coiled reinforcing member is disposed along a portion of the hollow elongate cannula and is adapted to provide structural support to the elongate cannula. A second coiled reinforcing member is disposed along a portion of the hollow elongate cannula and is adapted to provide structural support to the elongate cannula. An intermediate basket is disposed on the elongate cannula between the proximal end and the distal end and includes a forward edge, a rearward edge, and at least one rib extending between the forward edge and rearward edge. The intermediate basket also includes at least one protrusion extending orthogonally from the forward edge and at least one protrusion extending from the rearward edge. A distal basket has a front edge and a back edge. The distal basket is disposed at the distal end of the elongate cannula.

Yet another aspect of the present invention is a method for making a cannula assembly, including forming a thin sheet of metal and developing a pattern of reinforcement members in the thin sheet of metal. At least one rib having a predetermined width is formed in the reinforcing member. The reinforcement members are removed from the pattern. At least one of the reinforcement members is coiled into a reinforcing basket. A coiled reinforcing member having a terminal end is installed on the cannula assembly. An offset is created in the reinforcing basket. The reinforcement basket is installed so that the offset is adjacent to the terminal end of the coiled reinforcing member of the cannula assembly. A layer of material is installed over the reinforcement basket and the coiled reinforcing member.

These and other features, advantages and objects of the present invention will be further understood and appreciated by those skilled in the art upon studying the following specification, claims, and appended drawings.

BRIEF DESCRIPTION OF THE DRAWINGS

FIG. 2 is an enlarged perspective view of one embodiment of a distal end of a cannula assembly;

FIG. 2A is an enlarged perspective view of another embodiment of a distal end of a cannula assembly;

FIG. 3 is a partial front top perspective view of the distal end of the cannula assembly of FIG. 2;

FIG. 4 is a partial side elevational view of the distal end of a cannula assembly and introducer;

FIG. 5 is a partial side perspective view of the distal end of FIG. 4;

FIG. 6 is an enlarged side perspective view of the distal end of FIG. 4;

FIG. 7 is an enlarged side perspective view of the distal end of FIG. 4 with the introducer removed;

FIG. 11 is an enlarged partial side elevational view of the intermediate reinforcing band of FIG. 8;

FIG. 12 is a partial bottom perspective view of the intermediate reinforcing band of FIG. 8;

FIG. 13 is a partial enlarged bottom elevational view of another embodiment of an intermediate reinforcing band for use on a cannula assembly;

FIG. 14 is a side elevational view of an intermediate portion of a cannula assembly having multiple intermediate reinforcing bands.

DETAILED DESCRIPTION OF PREFERRED EMBODIMENTS

Figure 1:
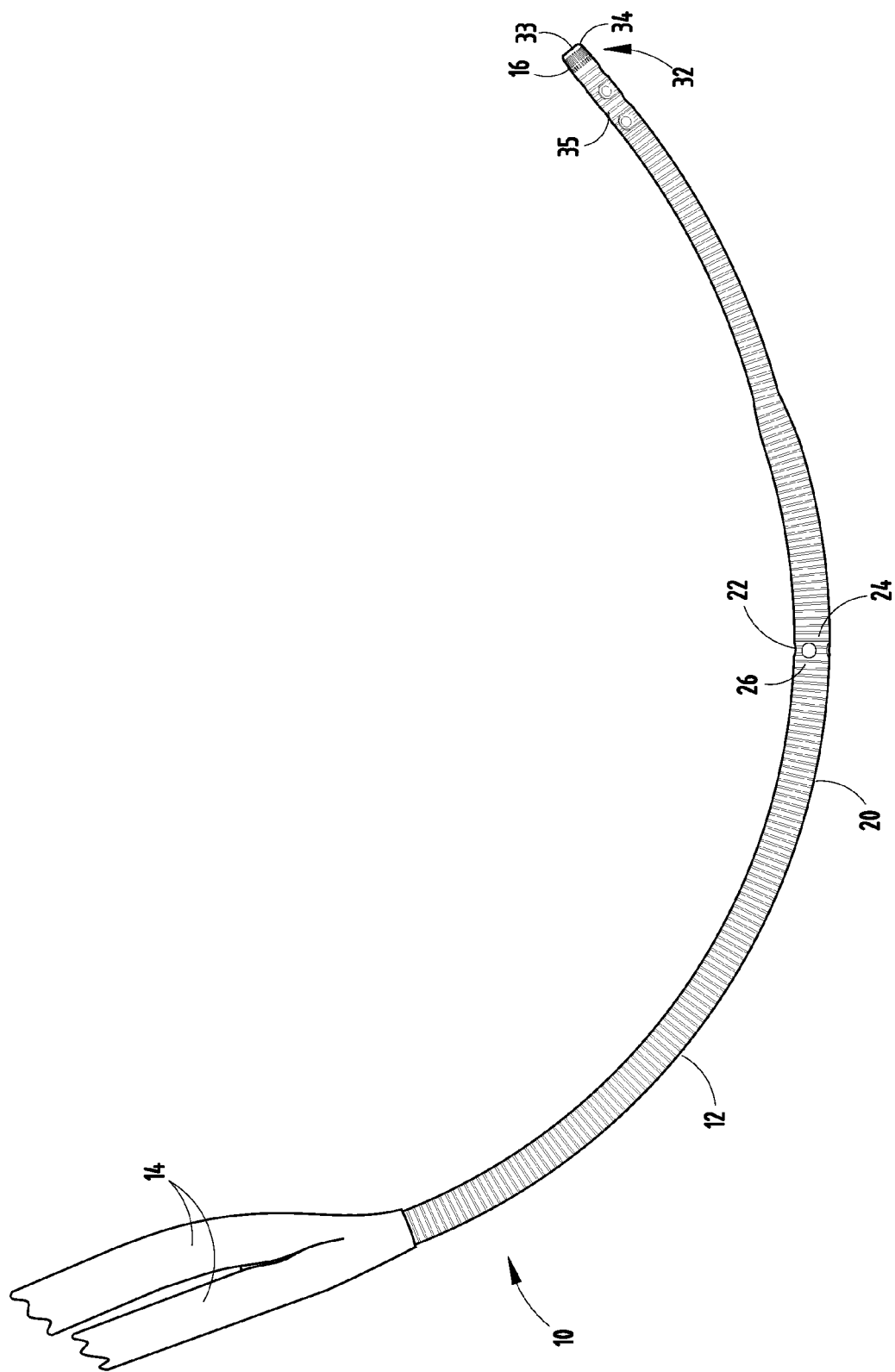
FIG. 1 is a top elevational view of one embodiment of a cannula assembly of the instant invention.

For purposes of description herein the terms "upper", "lower", "right", "left", "rear", "front", "vertical", "horizontal" and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

As illustrated in FIGS. 1 and 2, the reference numeral 10 generally designates a cannula assembly having a hollow elongate cannula 12 with a proximal end 14, a distal end 16, and a central axis 18. A coiled reinforcing member 20 is disposed along a portion of the hollow elongate cannula 12 and is adapted to provide structural support to the hollow elongate cannula 12 (FIG. 2). An intermediate reinforcing basket or reinforcing band 22 is disposed on the hollow elongate cannula 12 between the proximal end 14 and the distal end 16 and includes a forward edge 24, a rearward edge 26, at least one rib 28 and at least one spacing protrusion 30 (FIG. 10) extending orthogonally from the forward edge 24 and at least one spacing protrusion 30 extending from the rearward edge 26. A distal basket or reinforcing band 32 is disposed at the distal end 16 of the hollow elongate cannula 12 and has a front edge 33 and a back edge 35 and a plurality of fingers 34 that extend from the front edge 33 and taper slightly inward toward the central axis 18 of the hollow elongate cannula 12.

Referring to FIG. 2, the distal reinforcing band 32 illustrated is disposed at the distal end 16 of the cannula 10 and has multiple ribs 28. The distal reinforcing band 32 is located between layers 36 of a wall portion 38 of the cannula 10. More specifically, the distal reinforcing band 32 is inside the wall portion 38 of the cannula 10. The ribs 28 are located between the front edge 33 and the back edge 35 of the distal reinforcing band 32. The longitudinal extent of each rib 28 is substantially parallel with the front edge 33 and the back edge 35. The ribs 28 may include support columns 40 that extend orthogonal to the ribs 28. Any number of support columns 40 may be disposed about the circumference of the ribs 28, depending on the application and the desired rigidity and flexibility. The ribs 28 and support columns 40 may also have a non-orthogonal orientation, or be non-linear, helical, curved, etc.

Referring again to FIG. 2, the fingers 34 each include a base 42 and a tip 44. The base 42 of the fingers 34 extends orthogonally from the front edge 33. The tip 44 of each finger 34 terminates at or near the distal end 16 of the cannula 10. The tips 44 of the fingers 34 may be narrower than the base 42 and may taper slightly inward toward the central axis 18 of the cannula assembly 10. The fingers 34 provide stiffness to the cannula wall portion 38 while allowing the distal end 16 to expand radially outward or contract radially inward. This expansion and contraction is desirable when the cannula 10 is used with an internal stylet or introducer 53 (FIGS. 4 and 5) to allow a close sliding fit without binding or buckling. Accordingly, the distal end 16 of the cannula 10 can remain soft, flexible and atraumatic. In addition, the spacing protrusions 30 shown in FIG. 2 extend generally orthogonally from the back edge 35. The spacing protrusions 30 act as bumpers or spacers to prevent abutting contact of the back edge 35 with a terminal edge 46 (FIGS. 2 and 4) of the coiled reinforcing member 20. This construction eliminates structural weakness that occurs when the edges abut, and thus minimizes kinking and/or buckling that could occur when the cannula 10 is placed in a flexed state.

FIGS. 4-7 illustrate another embodiment of a distal reinforcing band 32A having ports 54A. As previously mentioned, the introducer 53 may be used in conjunction with the cannula 10. When the introducer 53 is provided, the distal end 16 may expand radially outward by stretching the material between the fingers 34A to accommodate the thickness of the introducer 53. It is contemplated that any of the embodiments in co-pending related application INTRODUCER FOR CANNULA AND METHOD, the entire contents of which are incorporated herein by reference, could be used with cannula 10. The distal end 16 of the cannula 10 wraps around the introducer 53, as shown in FIG. 6, and when the introducer 53 is removed, the fingers 34A and tension in the wall cause the distal end 16 to contract radially inwardly (FIG. 7).

The illustrated distal basket 32 of FIG. 2A includes a back edge 35 that is substantially circular. Corners 49, formed at the junction of back edge 35 and distal basket edges 50, 51 are substantially aligned and are spaced equidistant from the terminal edge 46 of the coiled reinforcing member 20. Alternatively, the corners 49 may be staggered to create an offset as discussed in further detail below.

As shown in FIGS. 4-7, an offset 58A may be disposed on the back edge 35A of the distal reinforcing band 32A that is designed to align with a forward terminal end 59 of the coiled reinforcing member 20 and is adapted to abut the forward terminal end 59 of the coiled reinforcing member 20 in the cannula assembly 10. The alignment of the offset 58A and forward terminal end 59 provides a smooth transition from the coiled reinforcing member 20 to the distal reinforcing band 32A, thereby minimizing the likelihood of kinking or buckling at or near the offset 58A. A width W1 of the offset 58A will generally be equal to a width W2 of the forward terminal end 59 (FIGS. 6 and 7). Alternatively the widths W1, W2 may be of differing sizes depending on the construction and arrangement of the distal reinforcing band 32A. At least one protrusion 30 extends orthogonally from the back edge 35A. At least one rib 28A is disposed between the front edge 33A and the back edge 35A and extends substantially parallel with the front and back edges 33A, 35A. The fingers 34A extend generally orthogonally from the front edge 33A although it is conceived that the fingers 34A could extend at various angles or have a curvilinear design. Each finger 34A has a tip 44A that extends from base 42A and that tapers slightly toward the central longitudinal axis 18 of the cannula assembly 10.

Figure 8:
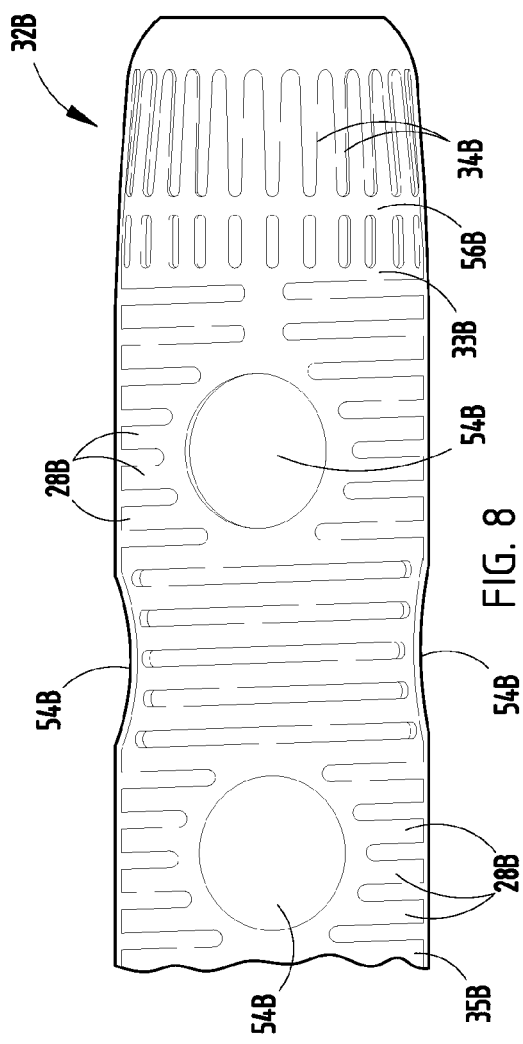
FIG. 8 is a partial top elevational view of another embodiment of a distal end of a cannula assembly.
Figure 9:
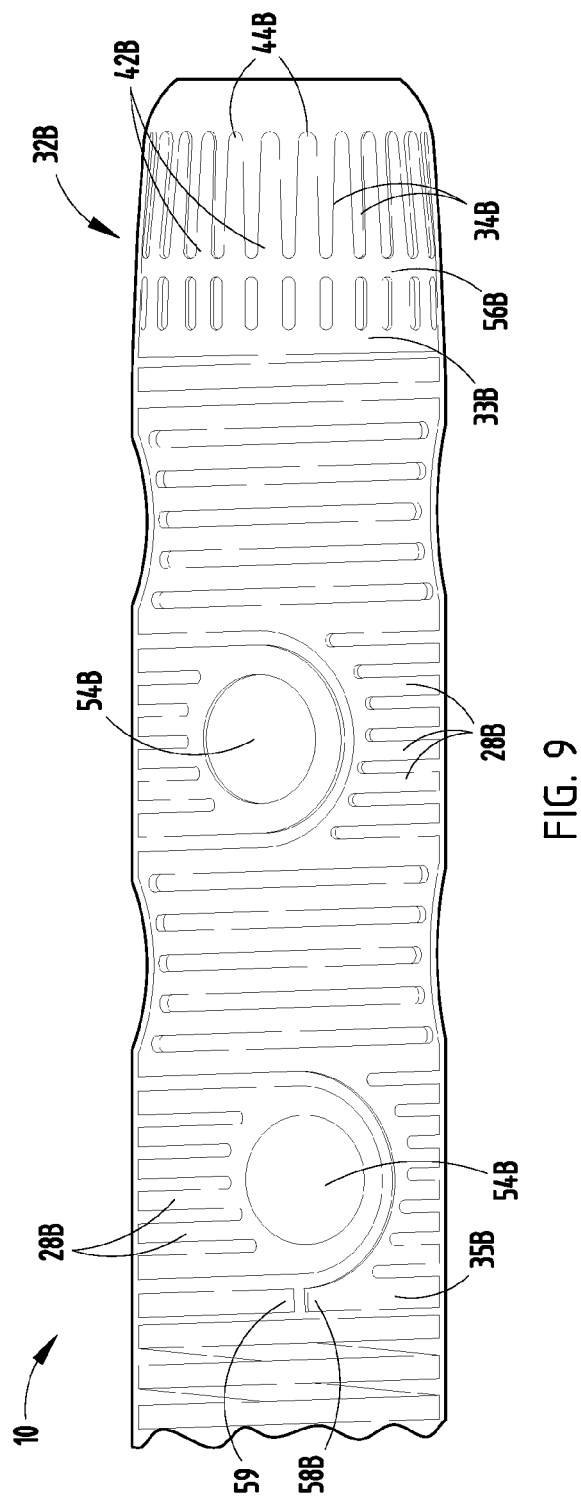
FIG. 9 is an enlarged side elevational view of the distal end shown in FIG. 8.

FIGS. 8 and 9 illustrate another embodiment of a distal reinforcing band 32B that incorporates ports 54B for introduction or drainage of fluid to or from the body of a patient, respectively. The ports 54B are offset more evenly to spread structural support around the cannula 10. The distal reinforcing band 32B of FIGS. 8 and 9 also illustrates a circumferential finger support 56B connecting the fingers 34. The finger support 56B provides structural rigidity to the fingers 34, which taper inward toward the central longitudinal axis 18 of the cannula assembly 10. An offset 58B for the distal reinforcing band 32B may be provided as shown in FIG. 9. The distal reinforcing band 32B also has fingers 34B with bases 42B and tips 44B.

Figure 10:
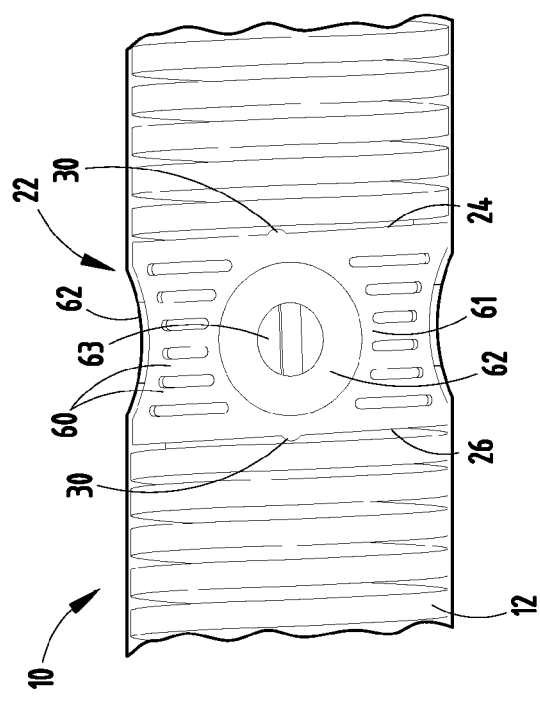
FIG. 10 is an enlarged partial top perspective view of one embodiment of an intermediate reinforcing band installed in a cannula assembly of the instant invention.
Figure 10A:
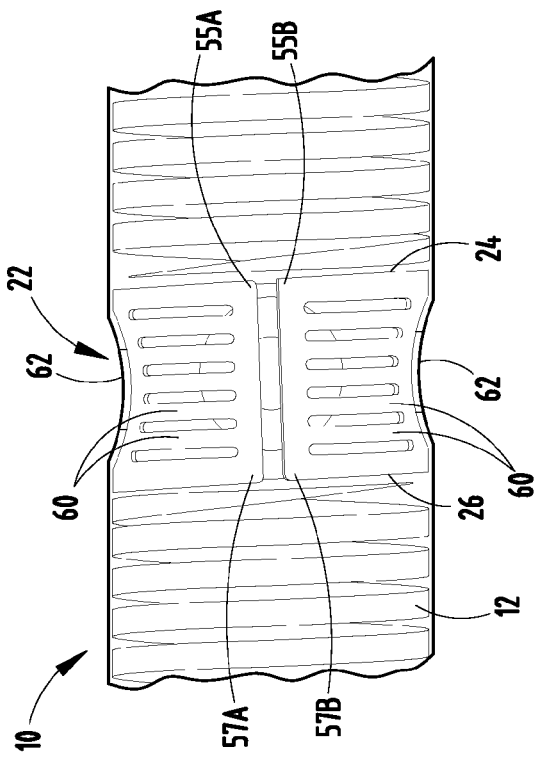
FIG. 10A is an enlarged partial bottom perspective view of another embodiment of an intermediate reinforcing band of a cannula assembly of the instant invention.

The example shown in FIGS. 10 and 10A illustrates an intermediate reinforcing band 22 for the cannula assembly 10 that has an aligned and planar forward edge 24 and rearward edge 26, such that no offset is present. The corners 55A, 55B are substantially aligned as are the rearward edges 57A, 57B so that the intermediate reinforcing band 22 is substantially cylindrical in shape. The hollow body of the intermediate reinforcing band 22 includes multiple ribs 60 and multiple rims 61 that define ports 62. The ports 62 are sized and spaced to allow one or more appropriately sized apertures 63 to be created in the cannula 10. The apertures 63 are formed by removing a segment of wall portion material from the wall portion 38 that overlies and/or underlies the port 62. The wall portion material is removed from the wall portion 38 by drilling, punching, or other means. The ports 62 may be used for drainage or infusion, depending on the application. The ribs 60 connect with each rim 61. Several spacing protrusions 30 may be present on the intermediate reinforcing band 22, as shown in FIG. 10. Alternatively, as shown in FIG. 10A, the spacing protrusions may be omitted. At least one rib 60 is disposed between the forward edge 24 and the rearward edge 26 and extends substantially parallel with the forward and rearward edges 24, 26.

The illustrated intermediate reinforcing band 22 of FIGS. 11 and 12 includes a forward offset 64 disposed on the forward edge 24 of the intermediate reinforcing band 22. Similar to the offset 58 of the distal reinforcing band 32 described above, the forward offset 64 is aligned with a rearward terminal end 65 to provide a smooth transition in cannula support from the coiled reinforcing member 20 to the intermediate reinforcing band 22, thereby minimizing the likelihood of kinking or buckling at or near the forward offset 64. The forward offset 64 may have a width W3 that is substantially equal to a predetermined width W4 of the rearward terminal end 65 of the coiled reinforcing member 20, although this depends on the arrangement and construction of the intermediate reinforcing band 22.

Referring again to FIGS. 10-12, the illustrated intermediate reinforcing band 22 includes a rearward offset 66 disposed on the intermediate reinforcing band 22. The rearward offset 66 is aligned with a forward terminal end 68 to provide a smooth transition in cannula support from the intermediate reinforcing band 22 to the coiled reinforcing member 20, thereby minimizing the likelihood of kinking or buckling at or near the rearward offset 66. The rearward offset 66 may have a width W5 that is substantially equal to a predetermined width W6 of the forward terminal end 68 of the coiled reinforcing member 20 although this depends on the arrangement and construction of the intermediate reinforcing band 22. At least one protrusion 30 (FIG. 8) may extend orthogonally from the forward or rearward edge 24, 26.

The distal and intermediate reinforcing bands 32, 22 may be constructed of a variety of materials including stainless steel and other metals. In addition, engineered plastics could also be used.

FIGS. 13 and 14 illustrate another embodiment for an intermediate reinforcing band 22A installed at more than one site on a single cannula assembly 10. The intermediate reinforcing band includes forward offset 64A and rearward offset 66A. The forward offset 64A is aligned with and has substantially the same width as the combined width of a first end portion 69 and rearward terminal end 65A with appropriate spacing as needed. Similarly, the rearward offset 66A is aligned with and has substantially the same width as the combined width of a second end portion 69 and forward terminal end 68A with appropriate spacing as needed. The reinforcing band 22A also includes multiple ribs 60A and multiple rims 61A that define ports 62A. The ports 62A are sized and spaced to allow one or more appropriately sized apertures 63A to be created in the cannula 10.

Figure 15:
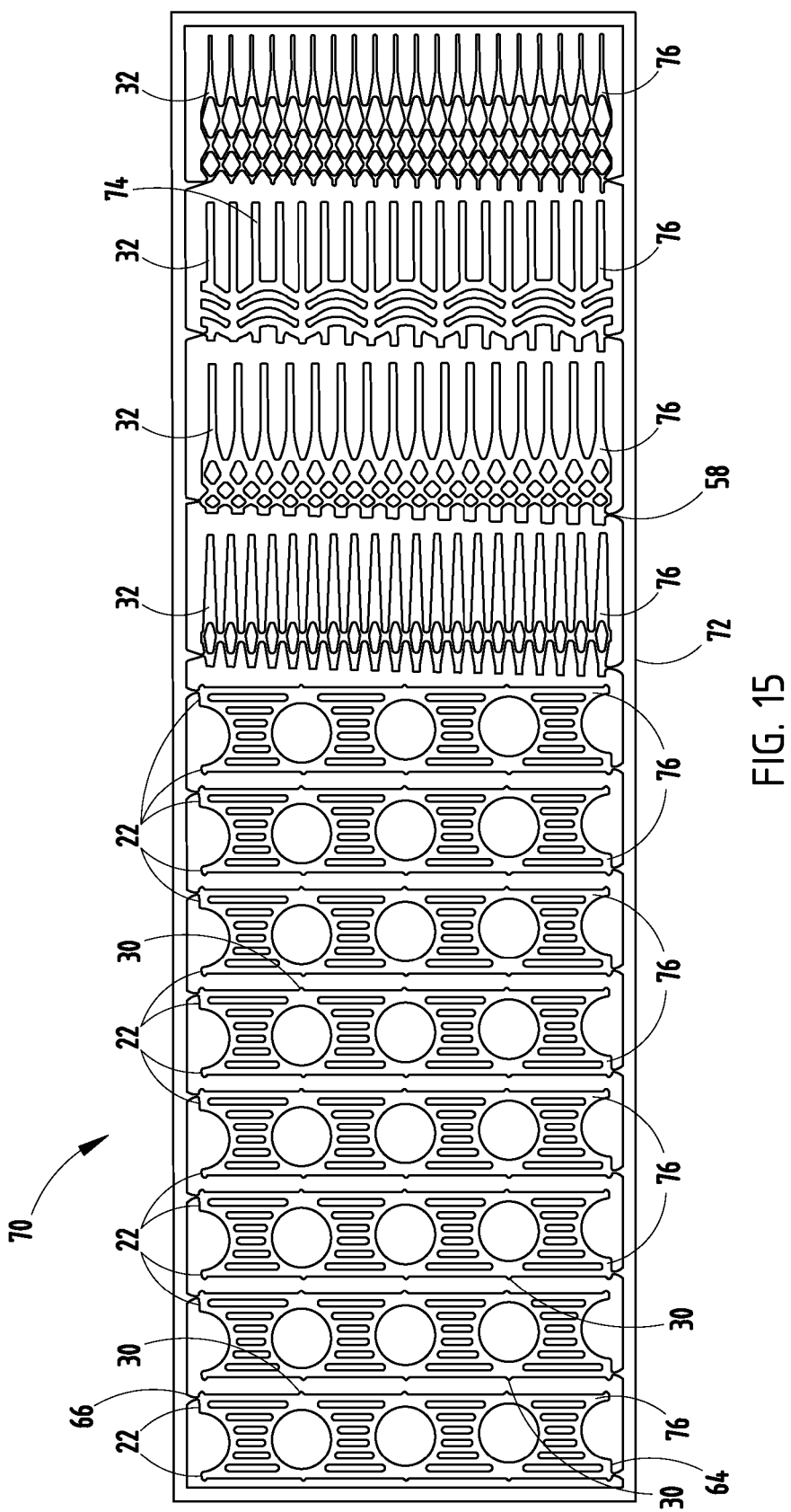
FIG. 15 is an enlarged top elevational view of a variety of cannula reinforcing bands after making but prior to forming.

Referring now to FIG. 15, multiple patterns 70 may be used to create various distal and intermediate reinforcing bands 32, 22. To make a cannula assembly 10 a thin sheet of metal 72 is formed and a pattern 74 is developed on the thin sheet of metal 72 that outlines individual pre-formed reinforcement sections 76. A spacing protrusion 30 may be provided on the individual reinforcement sections 76. The thin sheet of metal 72 is photo etched or laser cut to define the individual reinforcement sections 76. The individual reinforcement sections 76 are attached to the pattern 74 at limited locations and are ultimately removed from the pattern 74. The reinforcement sections 76 are then coiled into a reinforcing band 22 or 32 as shown in FIGS. 2 and 10, respectively. Ribs 28 may be formed on the reinforcing band 22, 32 and have a predetermined width. An offset 58, 64, 66 may be created in the reinforcing band 22, 32. A coiled reinforcing member 20 is installed on the cannula assembly 10 and has at least one terminal end. The reinforcing band 22, 32 is installed on the cannula assembly 10 so that the offset 58, 64, 66 is adjacent to one of the terminal ends of the coiled reinforcing member 20. A layer of material is installed over the reinforcing band 22, 32 and the coiled reinforcing member 20 of the cannula assembly 10.

It should be understood that the reinforcing bands 22, 32 can be used with many cannula constructions, including those disclosed in co-pending application entitled COAXIAL VENAL CANNULA AND METHOD, the entire contents of which are incorporated herein by reference.

The above description is considered that of the preferred embodiments only. Modifications of the invention will occur to those skilled in the art and to those who make or use the invention. Therefore, it is understood that the embodiments shown in the drawings and described above is merely for illustrative purposes and not intended to limit the scope of the invention, which is defined by the following claims as interpreted according to the principles of patent law, including the Doctrine of Equivalents.

What is claimed is:

1. A distal basket for a cannula assembly comprising:
    a cylindrical body portion installed in a wall portion of the cannula assembly adjacent a fully, open distal end of the cannula assembly, said cylindrical body portion having a circular first edge, a circular second edge, and a central axis extending through said cylindrical body portion;
    at least one rib disposed between said circular first edge and said circular second edge and extending substantially parallel with said first and second edges;
    a plurality of fingers extending orthogonally from said first edge toward said fully, open distal end, each of said fingers having a base and a distal end; and
    an offset disposed on said second edge of said cylindrical body portion and adapted to abut a distal terminal end of a coiled reinforcing member in the cannula assembly, said offset having a width substantially equal to a width of the distal terminal end of the coiled reinforcing member.

2. The distal basket for a cannula assembly of claim 1, further comprising:
    a spacing protrusion extending from said circular second edge.

3. The distal basket for a cannula assembly of claim 1, further comprising:

support columns extending between said circular first edge and said circular second edge.

4. The distal basket for a cannula assembly of claim 1, further comprising:
a circumferential finger support connected to said fingers.

5. The distal basket for a cannula assembly of claim 1, further comprising:
a spacing protrusion extending from said circular second edge.

6. The distal basket for a cannula assembly of claim 1, further comprising:
a circumferential finger support connected to said fingers.

7. The distal basket for a cannula assembly of claim 1, further comprising:
support columns extending between said circular first edge and said circular second edge.

8. A distal basket for a cannula assembly comprising:
a cylindrical body portion installed in a wall portion of the cannula assembly having a first edge, a second edge, and a central axis extending through said cylindrical body portion;
a plurality of distinct protrusions integral with said cylindrical body portion and extending orthogonally from said second edge;
at least one rib disposed between said first edge and said second edge and extending substantially parallel with said first and second edges;
a plurality of fingers extending orthogonally from said first edge, each of said fingers having a base and a distal end; and
an offset disposed on said second edge of said cylindrical body portion and adapted to abut a distal terminal end of a coiled reinforcing member in the cannula assembly, said offset having a width substantially equal to a width of the distal terminal end of the coiled reinforcing member.

9. The distal basket for a cannula assembly of claim 8, wherein:
said distal end of each finger tapers slightly toward the central axis.

10. The distal basket for a cannula assembly of claim 9, further comprising:
at least one port having an aperture extending orthogonally to said central axis.

11. An intermediate basket for a cannula assembly comprising:
a coiled cylindrical body portion installed in the cannula assembly and having a first edge, a second edge, and a central axis;
at least one rib disposed between and parallel with said first edge and said second edge having a predetermined width, the at least one rib being generally defined by first and second elongate apertures that are generally parallel with the first and second side edges;
at least one port having an aperture extending orthogonally to said central axis: and
a forward offset disposed on said first edge of said cylindrical body portion, said forward offset having a width substantially equal to the width of an adjacent terminal end of a coiled reinforcing member in the cannula assembly, such that said forward offset provides a smooth transition in cannula support from the intermediate basket to the coiled reinforcing member.

12. The intermediate basket of claim 11, wherein:
the intermediate basket is made from a coiled metal material.

13. The intermediate basket of claim 12, further comprising:
a rearward offset disposed on said second edge of said cylindrical body portion.

14. The intermediate basket of claim 13, further comprising:
at least one protrusion extending orthogonally from one of said first or said second edge.

15. The intermediate basket of claim 13, wherein:
said rearward offset has a width substantially equal to the predetermined width of a terminal end of a second coiled reinforcing member in the cannula assembly.

16. A cannula assembly comprising:
a hollow elongate cannula having a proximal end, an open distal end, and a central axis;
a first coiled reinforcing member disposed along a portion of said hollow elongate cannula and adapted to provide structural support to said elongate cannula;
a second coiled reinforcing member disposed along a portion of said hollow elongate cannula and adapted to provide structural support to said elongate cannula;
an intermediate basket disposed on said elongate cannula between said proximal end and said distal end and including a forward edge, a rearward edge, and at least one rib extending transversely across said intermediate basket between the forward edge and rearward edge substantially transverse to the central axis;
a distal basket having a front edge and a back edge, said distal basket including a plurality of fingers that extend from said front edge of said distal basket toward said open distal end and a plurality of protrusions extending from said back edge; and
an offset disposed on said back edge of said distal basket and adapted to abut a distal terminal end of a coiled reinforcing member in the cannula assembly, said offset having a width substantially equal to a width of the distal terminal end of the coiled reinforcing member.

17. The cannula assembly of claim 16, wherein:
said plurality of fingers taper slightly inwardly toward the central axis of said hollow elongate cannula.

18. The cannula assembly of claim 17, further comprising:
a spacing protrusion that extends from said forward edge of said intermediate basket.

19. The cannula assembly of claim 18, further comprising:
a spacing protrusion that extends from said rearward edge of said intermediate basket.

20. The cannula assembly of claim 19, wherein:
said forward and rearward edges of said intermediate basket include an offset such that said forward edge is configured to align with a rearward terminal end of said first coiled reinforcing member and said rearward edge is configured to align with a forward terminal end of said second coiled reinforcing member.

* * * * *